United States Patent [19]
Katzin

[11] Patent Number: 6,024,714
[45] Date of Patent: *Feb. 15, 2000

[54] DEFORMABLE ORTHOSIS

[75] Inventor: Leonard Katzin, deceased, late of Beverly Hills, Calif., by Josephine F. Katzin, legal representative

[73] Assignee: Lenjoy Engineering, Inc., Gardena, Calif.

[*] Notice: This patent is subject to a terminal disclaimer.

[21] Appl. No.: 08/992,524

[22] Filed: Dec. 17, 1997

Related U.S. Application Data

[62] Division of application No. 08/622,478, Mar. 26, 1996, Pat. No. 5,733,249.

[51] Int. Cl.[7] ............................. A61F 13/00; A61F 5/00
[52] U.S. Cl. ............................. 602/62; 602/21; 602/23
[58] Field of Search ............................. 602/20–22, 26, 602/64, 61, 6, 62; 118/578–880; 2/20, 21

[56] References Cited

U.S. PATENT DOCUMENTS

| | | | |
|---|---|---|---|
| 471,252 | 3/1892 | Hanley | 602/6 |
| 3,942,522 | 3/1976 | Wilson | 602/6 |
| 4,941,460 | 7/1990 | Working | 602/21 |
| 5,007,415 | 4/1991 | Marion | 602/26 |
| 5,248,292 | 9/1993 | Holland | 602/6 |
| 5,472,413 | 12/1995 | Detty | 602/20 X |
| 5,733,249 | 3/1998 | Katzin | 602/21 |

FOREIGN PATENT DOCUMENTS

| | | | |
|---|---|---|---|
| 94001066 | 1/1994 | WIPO | 602/21 |

*Primary Examiner*—Richard J. Apley
*Assistant Examiner*—Denise Pothier
*Attorney, Agent, or Firm*—Natan Epstein; Beehler & Pavitt

[57] ABSTRACT

Hand, knee and elbow orthosis each have a deformable semi-rigid stiffener having two end plates joined by a narrow midportion and contained between thin foam sheets to make an insert. A launderable cover of terry cloth fabric with permanently attached straps and a zippered opening fully envelops the insert. The hand orthosis has symmetrical left and right thumb extenders for ambidextrous application. The elbow and knee orthosis are symmetrical in length and width for convenient application insensitive to orientation of the orthosis on either a right or left limb.

4 Claims, 5 Drawing Sheets

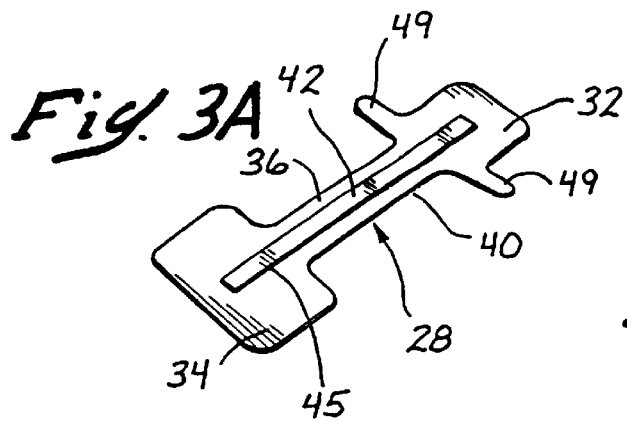
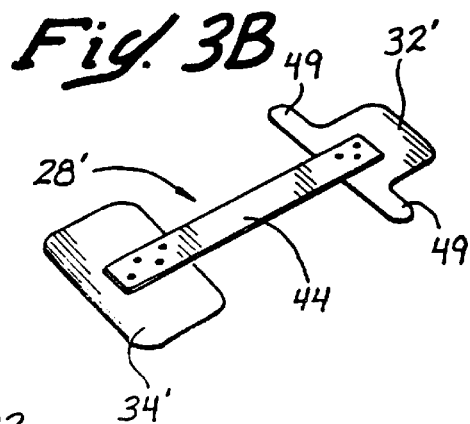
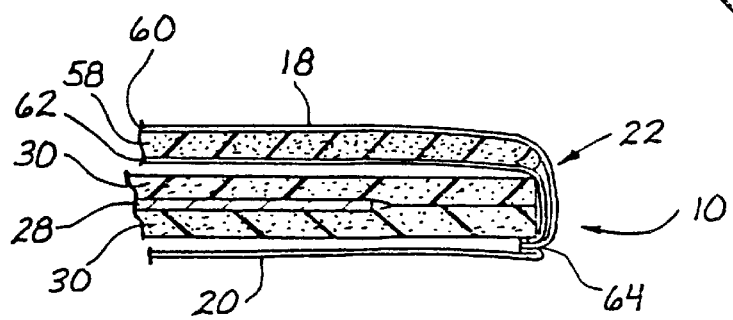
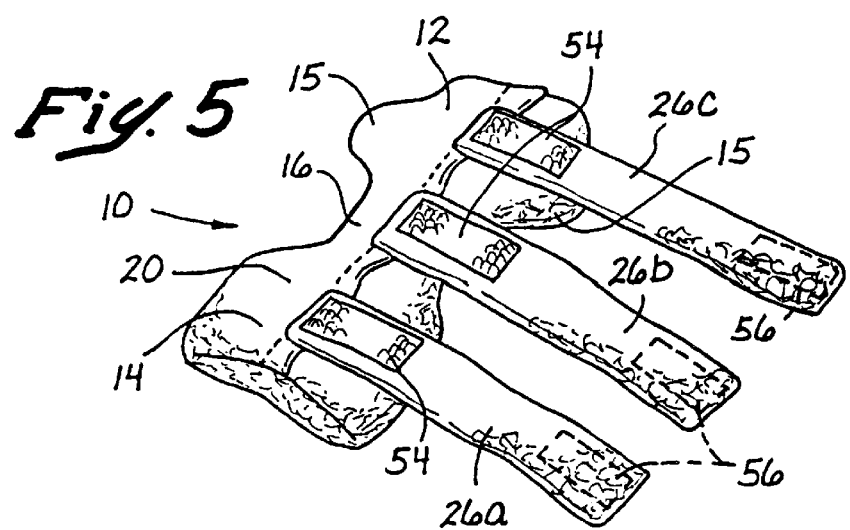

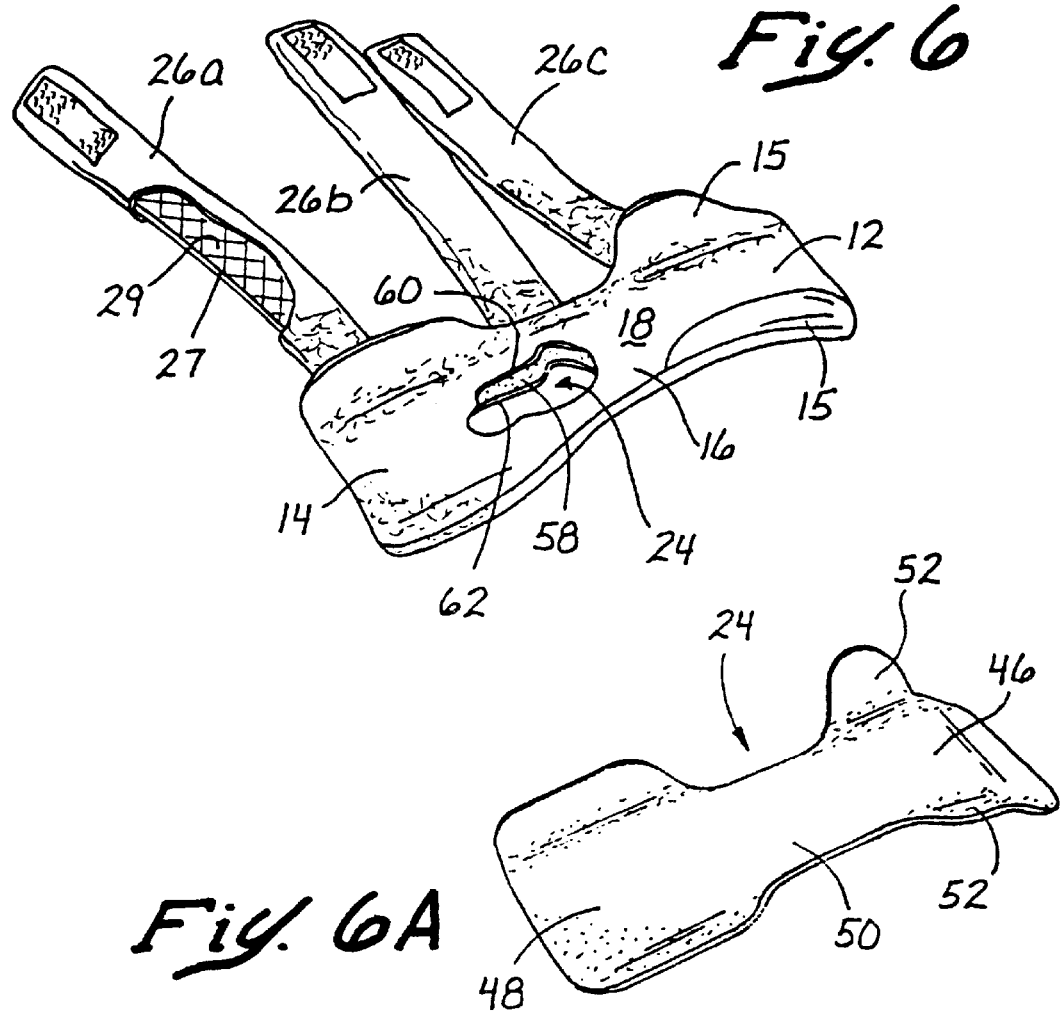
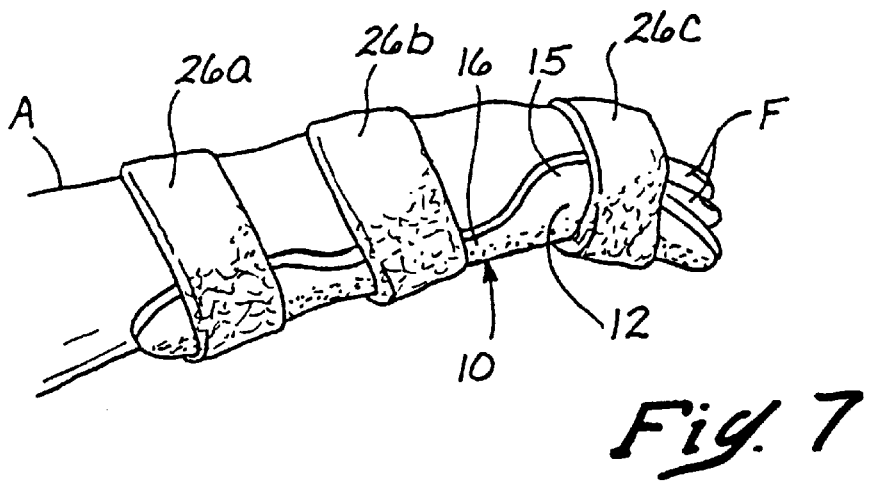

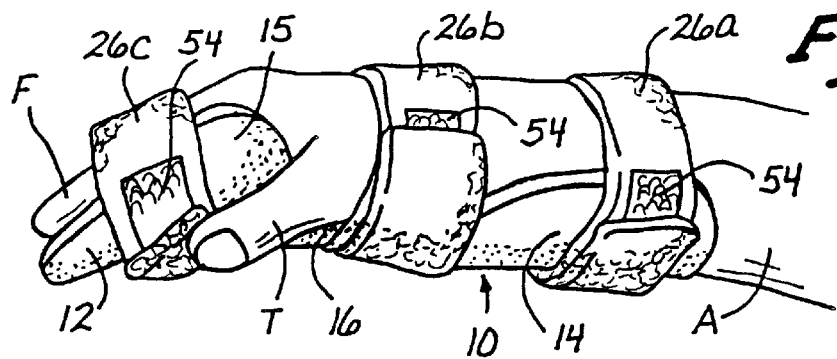
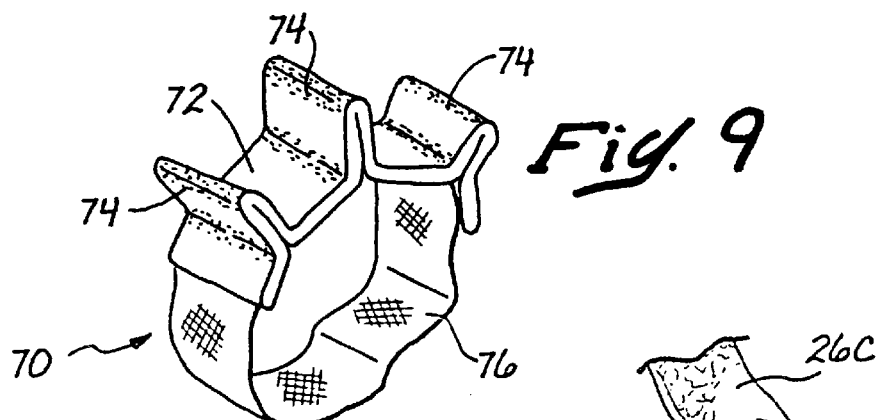
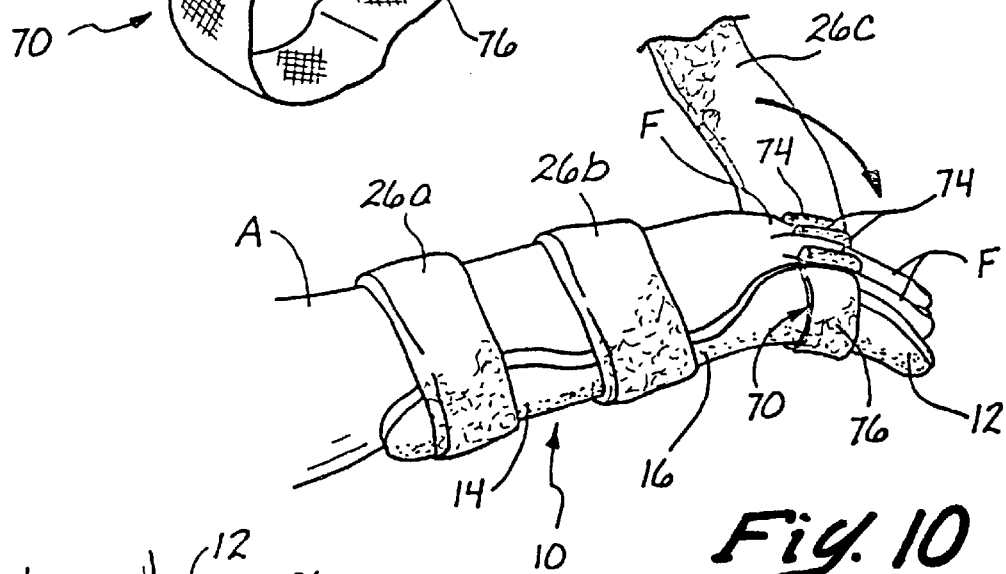
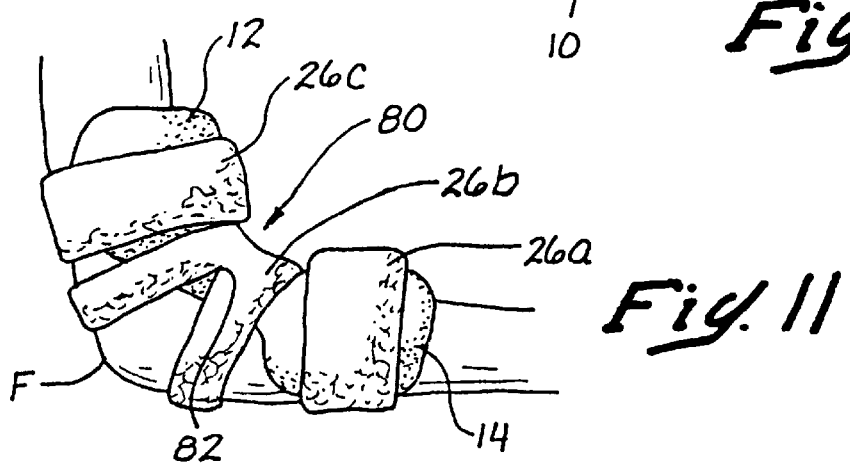

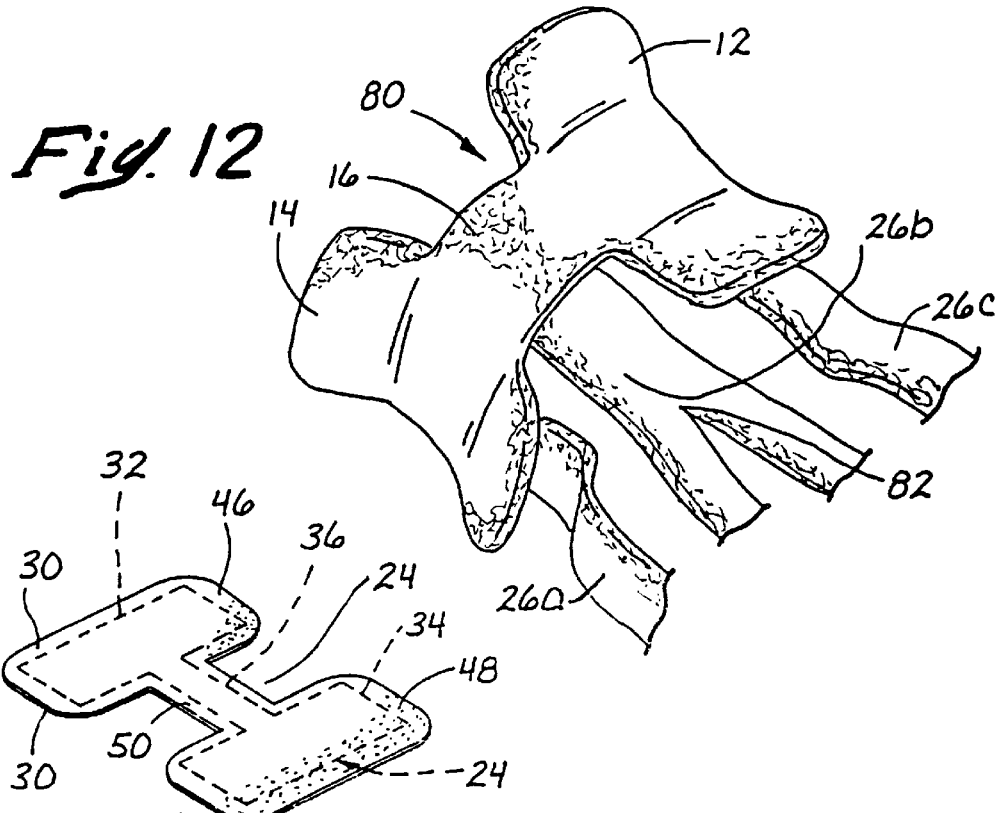
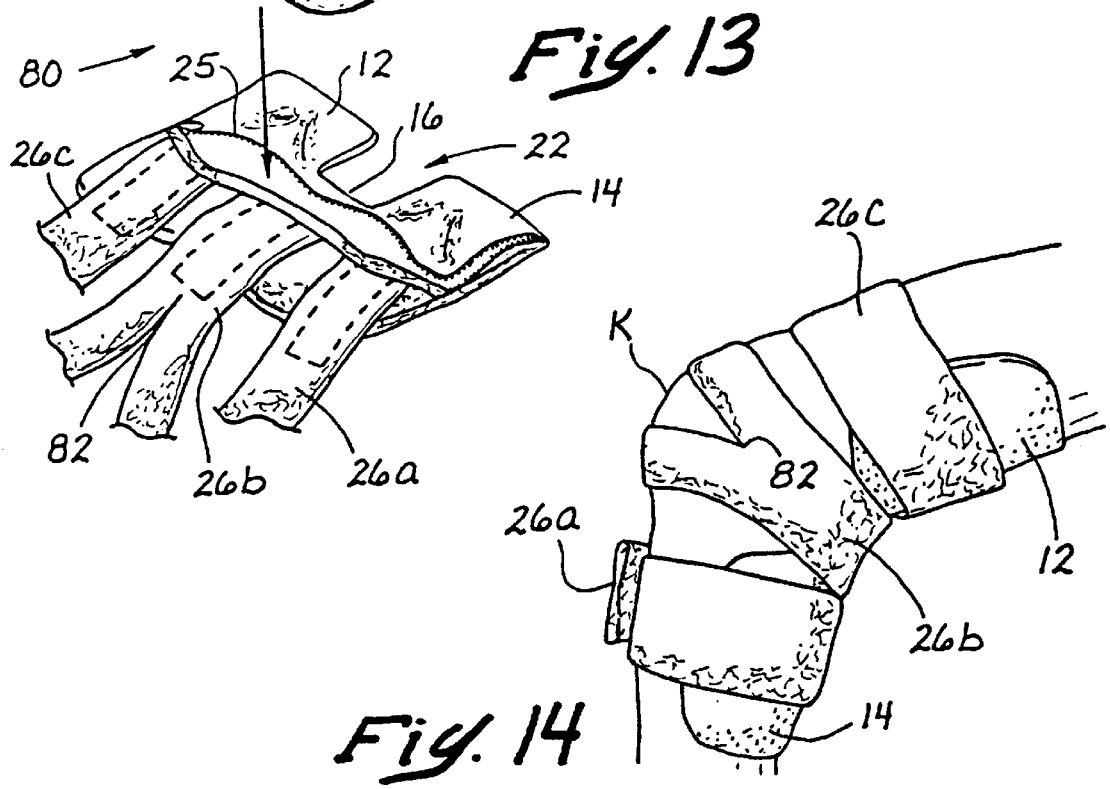

DEFORMABLE ORTHOSIS

This application is a division of U.S. application Ser. No. 08/622,478, filed Mar. 26, 1996, U.S. Pat. No. 5,733,249.

BACKGROUND OF THE INVENTION

1. Field of the Invention

This invention relates to orthopedic appliances and in particular to deformable splints for application to the elbow, hand or knee of a human patient to achieve a gradual, controlled extension of the limb to which it is applied.

2. State of the Prior Art

Persons debilitated by old age or chronic illness, particularly those bound to a wheelchair or bedridden, develop a tendency to retract their limbs to a persistently contracted condition. The arm, leg and hand are all susceptible to this affliction.

An accepted treatment for this condition is for a physical therapist to exercise the affected limb by flexing the pertinent joint through the range of motion possible under the circumstances, and applying light force to extend the limb slightly beyond the existing range of motion. The exercised limb is then fixed at the maximum achieved extension by means of an orthosis, or splint, which bridges the joint being exercised and prevents its retraction. This procedure is repeated during successive therapy sessions, over a period of weeks, to achieve a progressive extension of the limb. The orthosis is adjusted following each session to prevent the limb from retracting beyond the maximum extension gained during the particular session.

The nearest pertinent prior art is believed to be described in U.S. Pat. No. 5,248,292 issued to Holland, which discloses a static orthosis for use similar to the orthosis of this invention. Briefly, the Holland orthosis consists of a deformable unitary body having two pads connected by a spine. The unitary body is made up of an aluminum endoskeleton which is deformable by means of sufficient manual force and retains a desired shape when so deformed. The endoskeleton is molded in a closed cell polyethylene foam matrix. A unitary cover has pockets connected by a spine strap. Each pocket receives one of the end pads of the unitary body. A number of straps on the cover serve to attach the cover and the unitary body to the limb of the patient.

The Holland device suffers from a number of shortcomings. The removable cover does not entirely enclose the deformable unitary body, leaving exposed portions of the unitary body including edges which can press into the skin and tissues of the patient. This requires that the foam matrix around the aluminum endoskeleton provide cushioning. The exposed unitary body comes into contact with the patient and therefore must be periodically washed and cleaned, since the splint is worn for extended periods of time, often several weeks. The straps used to secure the splint to the patient's limb are attached directly to the unitary body, and are separate from the cover. Removal and reinstallation of the straps is needed for washing, adding complexity to the use of the device and exposing the straps to possible misplacement and loss.

Improved deformable static orthoses are needed featuring greater comfort and ease of use and maintenance.

SUMMARY OF THE INVENTION

The present invention addresses the aforementioned need by providing an improved orthosis for application to a joint of an anatomical limb. The improved orthosis has an insert with a semi-rigid stiffener deformable by application of manual force, the stiffener having first and second end plates joined to each other by a narrower intermediate strip, and opposing sheets of pliable material bonded to each other and defining a contour of the insert, such that the stiffener is completely contained between the opposing sheets. A removable cover of launderable fiber material is generally fitted to the contour of the insert. The cover has an interior accessible through a zippered opening for receiving the insert, so that the insert is fully enclosed and covered by the removable cover. A number of retaining straps are spaced apart on the cover and extend transversely to the intermediate strip of the insert for encircling the limb to which the orthosis is applied.

The stiffener is preferably metallic, such as of a soft steel, and the end plates are more readily deformable than the intermediate strip. The end plates may be of sheet metal such as a mild steel and the intermediate strip is desirably of thicker metal than the end plates. The end plates may be portions of a single metallic sheet which integrally includes a narrower mid-portion defining the intermediate strip, and the intermediate strip includes a reinforcing strip secured for increasing the stiffness of the mid-portion. The reinforcing strip may be narrower than the mid-portion, and the reinforcing strip may be welded to the mid-portion with welding material applied to define a tapered transition in thickness between the combined thickness of the reinforcing strip and the midportion, and the thickness of midportion alone. Alternatively, the end plates may be discrete metallic plates and the intermediate strip a metallic strip of greater stiffness than the discrete metallic plates.

The opposing sheets of the insert are desirably adhered directly to the metallic stiffener, and the opposing sheets may be of uniform thickness and foamed synthetic material. The outer covering is preferably made of terry-cloth material, which can be provided with compressible padding extending over at least one side of the insert, so that the opposing sheet do not need to provide significant cushioning. The covering may have two opposite sides, the zippered opening being on one of the opposite sides, and the other of the opposite sides being padded with cushioning material. The zippered opening preferably extends substantially the entire length of the cover in the direction of the intermediate strip. The insert preferably has a longitudinal axis along the intermediate strip and each of the end plates and the contour defined by the opposing sheets is symmetrical about the longitudinal axis, such that the orthosis is ambidextrous for application to either a right hand or a left hand limb.

In a hand orthosis according to this invention, one end plate of the stiffener has a central finger supporting portion of given width terminating in a forward edge. Two side portions project to a greater width at a location rearwardly spaced from the forward edge on each side of the finger supporting portion. Each side portion is individually bendable relative to the finger supporting portion for positioning as a separator between the thumb and the fingers of the hand, the side portions being symmetrical about the longitudinal axis of the insert such that the orthosis is ambidextrous for application to either a right or a left hand of a patient.

Each of the retaining straps may have hook and loop fasteners for securing each of the straps in encircling relationship with the limb to which the orthosis is applied. Each of said retaining straps may have an outer covering and an interior strip of compressible but non-stretchable padding material.

BRIEF DESCRIPTION OF THE DRAWINGS

FIG. 3A shows a first type of construction of the metallic stiffener of the deformable insert; and FIG. 3B shows a second type of construction of the metallic stiffener of the deformable insert;

FIG. 4 is a sectional view of the assembled splint taken along line 4—4 in FIG. 1;

FIG. 5 shows the bottom side of the cover zipped closed;

FIG. 6 is a view as in FIG. 1 showing the hand splint bent to a typical operative configuration;

FIG. 6A is perspective view of the deformable insert of the hand splint bent to the operative configuration of FIG. 6;

FIG. 7 is a right side view of the hand splint of FIG. 6 applied to the hand of a patient;

FIG. 8 is a left side view of the hand splint of FIG. 7;

FIG. 9 is a perspective view of a finger separator accessory for use with the hand splint of FIGS. 1 through 8;

FIG. 10 illustrates typical installation and use of the finger separator of FIG. 9 with the hand splint applied as in FIG. 7;

FIG. 11 shows an elbow splint according to this invention, applied to the elbow of a patient;

FIG. 12 is a perspective view of the proximal side of an elbow or knee splint, bent to a typical shape for application to the elbow of a patient as in FIG. 11 or a knee as in FIG. 14;

FIG. 13a shows the insert and cover of an elbow or knee splint, in original planar condition; and FIG. 14 illustrates application of the knee splint according to this invention to the knee of a typical patient.

DETAILED DESCRIPTION OF THE PREFERRED EMBODIMENTS

Figure 1:
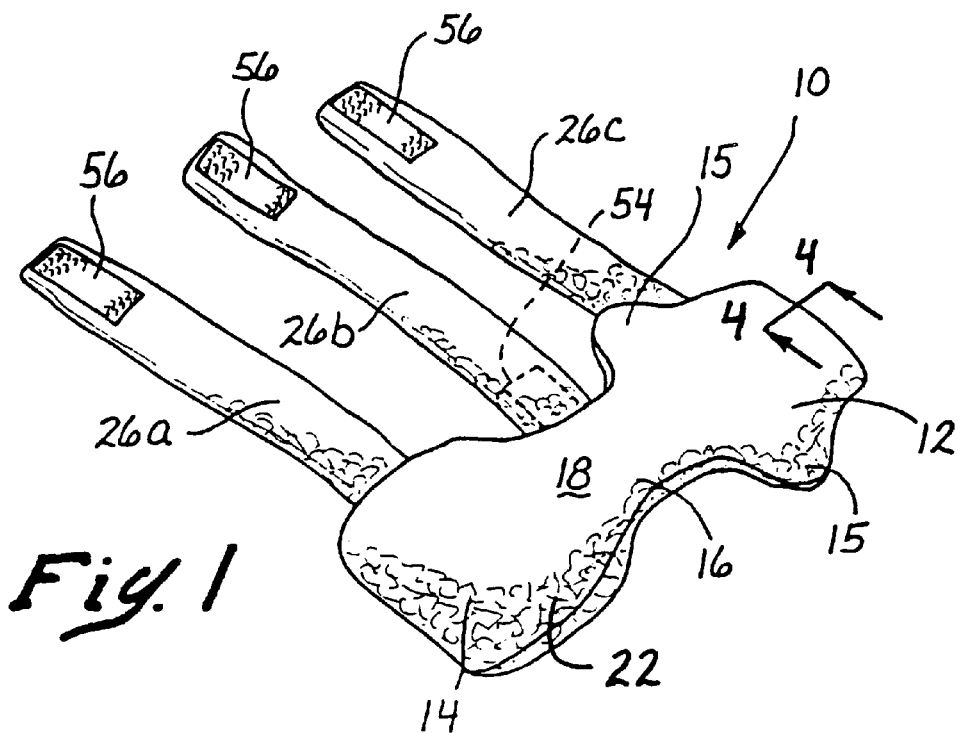
FIG. 1 is a top perspective view of a hand splint according to this invention, shown in an initial planar configuration.

With reference to the accompanying drawings, FIG. 1 shows a deformable static orthosis or splint, generally designated by the numeral 10, which by way of example is a hand splint adapted for application to the hand, wrist and forearm of a human patient. FIGS. 2 through 9 further illustrate the hand orthosis. The invention is not, however, limited to hand orthosis and the improvements described herein are equally applicable to elbow and knee splints, such as are shown in FIGS. 11 through 14.

The hand splint 10 in FIG. 1 has a cover 22 shaped to define two pads, including a front pad 12 and a rear pad 14, which are joined by a narrower waist section 16, arranged along a longitudinal axis which traverses all three portions of the splint. The splint further has a proximal side 18 which is applied against the limb of the patient, and an opposite, distal side 20, seen in FIGS. 4, 5 and 6, which faces away from the same limb.

Figure 2:
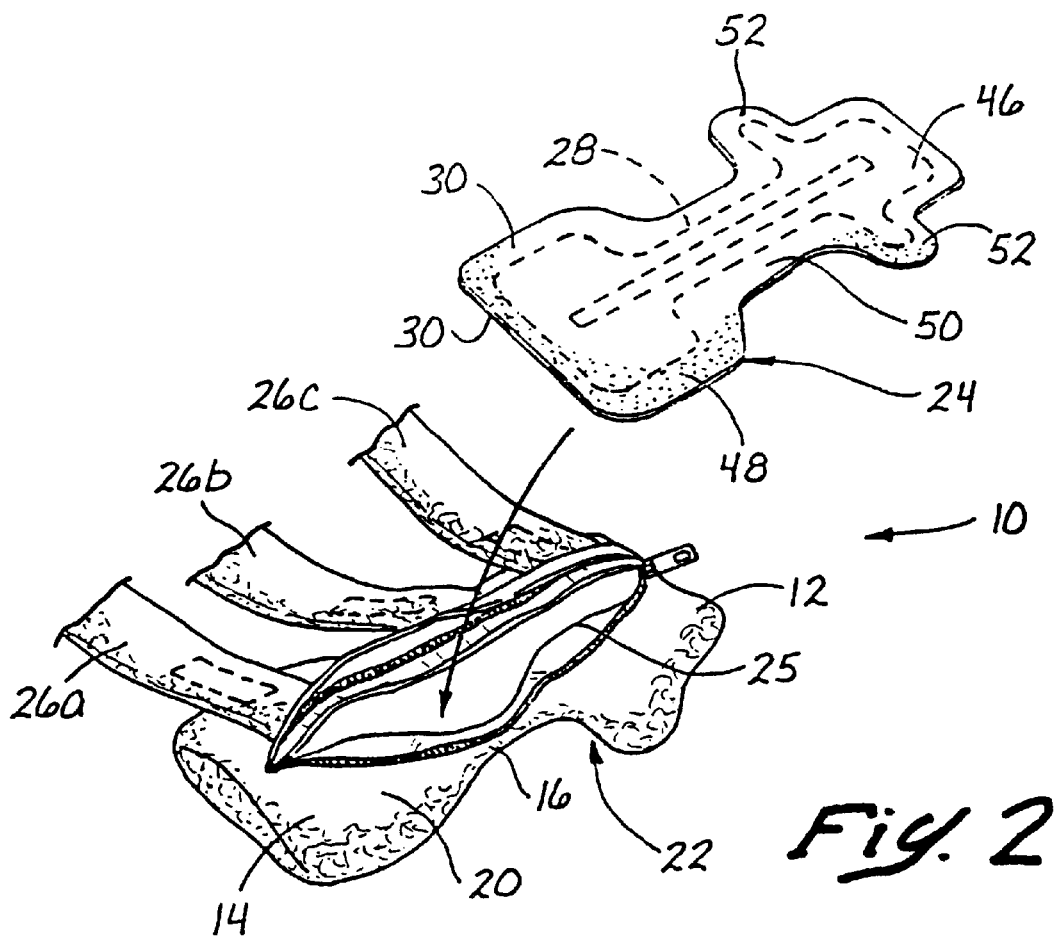
FIG. 2 is an exploded view of the hand splint of FIG. 1, showing the bottom side of the cover unzipped for access to its interior and the deformable insert in position for placement in the cover.

Turning to FIG. 2, it is seen that the orthosis 10 includes an exterior cover 22 and a deformable inner 24. The cover 22 has a zippered opening 25 on the distal side 20 which extends nearly the entire length of the cover. Three retaining straps 26a, 26b and 26c each have one end attached to the distal side of the cover at spaced apart locations along the length of the cover.

The deformable inner 24 is made up of a stiffener 28, seen in phantom lining in FIG. 2, which is entirely contained or laminated between two relatively thin opposing sheets 30 of foamed synthetic material, as shown in FIG. 4. The stiffener 28 has two end plates, front end plate 32 and rear end plate 34, joined to each other by a narrower midportion 36. FIGS. 3A and 3B show alternate forms of the stiffener 28. In FIG. 3A the end plates 32, 34 and the midportion 36 are portions of a single plate 40 of uniform thickness. A reinforcing strip 42 is affixed longitudinally along the midportion 36. The plate 40 and strip 42 are of a mild steel and the plate is such that it can be bent by moderate manual force. The reinforcing strip is chosen to substantially increase the stiffness of the plate 40 along its midportion 36. The result is that the end plates can be bent in a direction transverse to the length of the stiffener with less effort than required to bend the stiffener along its midportion. A similar result is obtained in the stiffener 28' of FIG. 3B where separate end plates 32',34' are connected by a connecting strip 44 of heavier gauge than the end plate material.

In the insert of FIG. 3A the reinforcing strip is welded to the plate 40 with a substantially continuous bead of solder or weldment material 45 extending about the four sides of the strip 42. The bead 45 is applied so as to form a tapering transition between the greater thickness of the reinforcing strip and the thickness of the plate 40 around the strip. The tapering transition of bead 45 eliminates a sharp edge around the strip 42 which might press against the skin of the user even through the layers of a foam sheet 30 and the cover 22 and be injurious or uncomfortable to the patient.

The foamed sheets 30 are oversized with respect to the stiffener 28 and define a contour of the inner 24 which generally follows the contour of the stiffener 28, so as to define two end pads, front end pad 46 and rear end pad 48 connected by a narrower intermediate portion 50. The front end pad 46 has a central finger supporting portion 51 of given width and terminating in a forward edge 53, and side wings 52 extending in opposite directions transversely to the longitudinal dimension of the inner 24, corresponding to wings 49 on the front plate 32 and 32' of the stiffener. It will be appreciated from FIGS. 1–10 that the side wings 52 extend to a greater width than the given width of the finger supporting portion 51 at a location rearwardly spaced from the forward edge 53 on each side of the finger supporting portion. The cover 22 is made of launderable and moisture absorbent terry-cloth fabric, preferably of natural cotton fiber, which entirely covers and contains the deformable inner 24. The cover 22 generally conforms to the perimeter and both sides of the inner 24. The inner 24 is inserted through the zippered opening 25 so that the front end pad 46 fits into the front pad 12 of the cover and the rear end pad 48 fits into the rear pad 14 of the cover. The midportion of the inner is contained by the waist portion 18 of the cover. The assembled splint 10, with the inner 24 inserted into the cover 22 and the zippered opening 25 closed, is seen in FIG. 5.

The inner 24 is in an initially planar condition as shown in FIG. 2, and is fitted to a particular patient by bending in both longitudinal and transverse directions, as suggested in FIG. 6A, to the contour of the limb to which it is to be applied. The inner 24 retains the shape to which it is formed and imparts a similar shape to the cover as in FIG. 6. Fitting of the splint 10 is normally done with the inner 24 contained inside the cover 22. Typically the proximal side 18 of the splint 10 will have a concave curvature at the end pads 12, 14 in a transverse direction and a convex curvature along the waist portion 18 in a longitudinal direction of the splint.

The hand splint 10 is applied as shown in FIGS. 7 and 8. The proximal side 18 of the splint is applied against the underside of the patient's arm A such that the front end pad 12 supports the fingers of the hand, the rear end pad 14 lies against the forearm, and the waist 18 lies under the wrist. The splint 10 is secured to the arm A in this position by wrapping each of the three retaining straps 26a–c around the forearm and hand and securing the free end of each strap to the distal side 20 of the cover by means of mating hook and loop fasteners 54, 56. As therapy progresses, the curvature of the waist portion 18 is gradually reduced to achieve extension of the hand and wrist from an initially retracted condition. The materials of which stiffener 28 is constructed are chosen so that the stiffener, and consequently the splint 10, can be formed to the desired shape by deliberate manual force applied by a therapist, but yet will resist forces to which it is normally subjected when worn by a patient. Neither the opposing sheets 30 nor the cover 22 contribute materially to the stiffness, i.e. resistance to deformation, of the splint 10.

The terry cloth cover 22 of splint 10 is padded on the proximal side 18 by a layer of compressible synthetic foam 58 contained between a outer sheet 60 of terry cloth cover material and an inner liner 62 which is also of similar terry cloth fabric. The three layers 60, 58, 62 extend over the entire proximal side 18 of the cover and are sewn together along the perimeter 64 of the cover. The foam padding 58 cushions contact of the patient's arm against the relatively firm inner 24, and particularly contact against the edges of the opposing foam sheets 30 which if unprotected would tend to cause some discomfort to the patient when firmly applied against the limb for extended periods of time.

Each of the retaining straps 26a–c are made of the same terry-cloth fabric as the cover 22, and is padded with a strip of resilient compressible non-stretchable synthetic foam which extends substantially the entire length of the strap and is entirely wrapped and covered by the terry-cloth fabric. The terry-cloth covering of retaining strap 26a is partially broken away in FIG. 6 to illustrate the foam strip 27. The foam strip is made non-stretchable by virtue of a mesh 29 of inelastic fiber bonded to one longitudinal surface of the strip. Such foam material is a commercially available product. The same padding is provided in each of the straps 26b and 26c. The padded retaining straps further reduce the likelihood of injury or discomfort to the patient when the splint is properly applied by a skilled therapist.

It will be appreciated that the cover 22 and retaining straps 26a–c are permanently secured together as a unit which can be easily separated from the inner 24 and washed, cleaned or laundered without concern with separation or loss of the straps apart from the cover. The synthetic foam surfaces of the inner 24 can also be easily cleaned or sanitized by methods appropriate to synthetic foam materials apart from the textile fabric of the cover 22. After cleaning the cover and inner are assembled quickly and easily, as already described.

The side wings 52 of the inner 24 extend into corresponding lateral extensions 15 formed in the cover 22, which are typically bent upwards from the proximal side 18 of the splint, as best understood from FIGS. 6 and 6A. The side wings 52 are deformed to the desired position while inside the cover 22, as in FIG. 6. The inner 24 is shown outside the cover in FIG. 6A for purposes of explanation only. The lateral extensions 15 constitute thumb extenders which serve to separate and extend the patient's thumb T away from the fingers F, as best understood by reference to FIG. 8. The position of the thumb extenders 15 can be gradually adjusted during the course of therapy to achieve gradual extension of the thumb.

The hand orthosis 10 is bilaterally symmetrical about a longitudinal axis dividing the front, rear and midportion of the splint. This symmetry makes the splint 10 ambidextrous, i.e., permits the hand splint to be applied equally to the right or the left hand of a patient, and eliminates the need to purchase and maintain stocks of separate right and left hand orthoses, with consequent reduction in administrative costs and improved efficiency of health care institutions where such splints are used. In particular, each splint has a left and a right side thumb extender 15, symmetrically disposed about the imaginary longitudinal axis, only one of which is used for a particular hand of the patient.

FIG. 9 shows an accessory finger separator 70 for use with the hand splint 10. The finger separator 70 has an upper portion 72 of terry cloth fabric folded and sewn to make three upright partitions 74. the opposite ends of the terry cloth upper are connected by an elastic band 76. The separator 70 is fitted onto the splint so as to encircle the front pad 12, as depicted in FIG. 9, such that the terry cloth upper 72 extends across the proximal side of the front pad and the elastic band 76 is stretched over the distal side of the front pad. The separator 70 is held on the splint 10 by elastic tension of the band 76. The fingers F of the patient are spaced from each other by the three partitions 74, each partition being inserted between each pair of adjacent fingers. Separation of the fingers is desirable in some cases to prevent deformations, ulcerations and other disease processes of the skin and joints when a patient's fingers are pressed together for extended periods of time.

The separator 72 is typically positioned forwardly of the thumb extenders 15 and forwardly of the front retaining strap 26c. However, the actual position of the separator 70 on the splint is easily adjusted, forwardly and backwardly as well as side to side, on the front pad 12, for optimum positioning as required by the shape, size and condition of the individual patient's hand. The ability to install or entirely remove the finger separator 70 on a hand splint 10 gives the therapist flexibility during the course of therapy while minimizing the cost of providing a finger separator when needed on an existing hand splint.

FIGS. 12 and 13 show a splint 80 which is shaped for use as an elbow or knee splint. The construction of splint 80 is similar to that of the hand splint 10 explained above, in that splint 80 also has a deformable inner contained and fully enclosed in a terry cloth cover, and numerals in FIGS. 11 through 14 designate features denoted by like numerals in FIGS. 1 through 8. The elbow and knee splint 80 differs from hand splint 10 in that no thumb extenders are needed nor provided, and the two end plates of splint 80 are similar to each other, so that splint 80 is not only bilaterally symmetrical about a longitudinal axis but also symmetrical about a line transverse to the waist of the splint. The central retaining strap 26b is bifurcated at 82 to wrap on either side of the elbow E or knee K, as shown in FIGS. 11 and 14 respectively. The splint 80 is made in different sizes, a smaller size for application to the elbow and a larger size for the knee. The difference between the elbow and knee splints is however one of scale only. In FIG. 13 the cover 22 is shown open along its zippered opening 24 and the deformable stiffener is shown in its initial flat, planar condition and removed from the cover. In FIG. 12 the splint 80 is shown assembled and formed to a shape appropriate for application to a knee or elbow of a patient.

The several advantages and improvements described in connection with the hand splint are equally featured in the elbow and knee splint 80, including provision of padding integral to the removable cover and permanent attachment of the retaining straps to the same cover. The construction of the inner is similar as is the construction of the stiffener of the inner.

While a preferred embodiment of the invention has been described and illustrated for purposes of clarity and example, it should be understood that many changes, substitutions and modifications to the described embodiment will be apparent to those possessed of ordinary skill in the art in light of the foregoing disclosure without thereby departing from the scope and spirit of the present invention which is defined by the following claims.

What is claimed is:

1. An orthosis for a hand comprising:

an insert having a semi-rigid stiffener deformable by application of manual force, said stiffener having first and second end plates joined to each other by a narrower intermediate portion, said stiffener being laminated between opposing sheets of pliable material bonded to each other and defining a contour of said insert, said stiffener being completely contained between said opposing sheets;

a removable cover of launderable fabric generally fitted to said contour, said cover having an interior accessible through a zippered opening for receiving said insert, and a zipper attached to said cover for selectively opening and closing said opening, said insert being fully covered by said removable cover in an assembled condition of said orthosis; and at least three retaining straps spaced apart on said cover and extending transversely to a longitudinal axis of said stiffener for encircling knuckles, wrist and forearm respectively of a hand to which the orthosis is applied;

wherein one of said end plates has a finger supporting portion of given width terminating in a forward edge and side portions projecting to width greater than the finger supporting portion width from opposite sides of said finger supporting portion in mutually opposite directions transversely to said longitudinal axis, each of said side portions being rearwardly spaced from said forward edge and individually bendable relative to said finger supporting portion for positioning as a separator between the thumb and the fingers of the hand, said insert including said side portions being symmetrical about said longitudinal axis such that said orthosis is ambidextrous for application to either a right or a left hand.

2. An orthosis for application to a joint of an anatomical limb, comprising:

an insert having a semi-rigid stiffener deformable by application of manual force, said stiffener having first and second end plates joined to each other by a narrower intermediate portion, said plates and said intermediate portion being symmetrical about a longitudinal axis extending along said midportion and bisecting said plates and also symmetrical about a line transverse to and bisecting said midportion;

said stiffener being laminated between opposing sheets of pliable material bonded to each other and defining a contour of said insert, said stiffener being completely contained between said opposing sheets;

a removable cover of launderable fabric generally fitted to said contour, said cover having an interior accessible through a zippered opening for receiving said insert, and a zipper attached to said cover for selectively opening and closing said opening, said insert being fully covered by said removable cover in an assembled condition of said orthosis;

both opposing sheets for said removable cover generally conforming to the contour of said stiffener, such that the orthosis is ambidextrous for use on either a right or a left limb; and a plurality of straps attached to said cover for encircling the limb to which the orthosis is to be applied, said straps being substantially symmetrically located relative to said line transverse to the midportion.

3. An orthosis comprising a semi-rigid insert having opposite end plates joined by a narrower midportion, said plates and said intermediate portion being symmetrical about a longitudinal axis extending along said midportion and bisecting said plates and also symmetrical about a midpoint of said midportion;

a removable cover of launderable fabric for covering said insert, a plurality of straps secured to said cover for encircling the limb to which the orthosis is to be applied, said straps being substantially symmetrically located relative to said line transverse to the midportion;

wherein one of said end plates has a finger supporting portion of given width terminating in a forward edge and side portions projecting to width greater than the finger supporting portion width limited to a location rearwardly spaced from said forward edge on each of opposite sides of said one of said end plates in mutually opposite directions transversely to said longitudinal axis, each of said side portions being individually bendable relative to said finger supporting portion for positioning as a separator between the thumb and the fingers of the hand, said side portions being symmetrical about said longitudinal axis such that said orthosis is ambidextrous for application to either a right or a left hand.

4. The orthosis of claim 3 wherein said plurality of straps comprises an odd number of said straps, a middle one of said straps being located at said midpoint.

* * * * *